United States Patent

Shikano et al.

[11] Patent Number: 5,530,632
[45] Date of Patent: Jun. 25, 1996

[54] CORDLESS LIGHT SOURCE

[75] Inventors: Shuji Shikano; Misuzu Hasobe, both of Urawa; Yasuji Matsuoka, Tokyo, all of Japan

[73] Assignee: Moritex Corporation, Tokyo, Japan

[21] Appl. No.: 305,141

[22] Filed: Sep. 13, 1994

[30] Foreign Application Priority Data

Sep. 14, 1993 [JP] Japan .................. 5-056459 U

[51] Int. Cl.⁶ .................................................. A61C 5/00
[52] U.S. Cl. .................. 362/109; 362/157; 362/373; 362/804; 433/27; 433/29; 433/215; 315/119
[58] Field of Search .................... 362/157, 109, 362/32, 294, 373, 804; 433/27, 29, 215, 229; 315/86, 119

[56] References Cited

U.S. PATENT DOCUMENTS

| | | | |
|---|---|---|---|
| 4,356,534 | 10/1982 | Hattori | 362/804 |
| 4,415,952 | 11/1983 | Hattori et al. | 362/804 |
| 4,499,525 | 2/1985 | Mallory | 362/157 |
| 4,607,623 | 8/1986 | Bauman | 362/804 |
| 4,818,231 | 4/1989 | Steiner et al. | 433/215 |
| 4,850,669 | 7/1989 | Welker et al. | 362/157 |
| 4,933,816 | 6/1990 | Hug et al. | 362/294 |
| 4,947,291 | 8/1990 | McDermott | 362/295 |
| 5,001,608 | 3/1991 | Kehrli et al. | 362/294 |
| 5,093,763 | 3/1992 | Vanderschuit et al. | 362/18 |
| 5,318,009 | 6/1994 | Robinson | 362/157 |

FOREIGN PATENT DOCUMENTS

| | | |
|---|---|---|
| 5-30428 | 8/1993 | Japan . |
| 8606614 | 11/1986 | WIPO . |

*Primary Examiner*—James C. Yeung
*Assistant Examiner*—Sara Sachie Raab
*Attorney, Agent, or Firm*—Brown, Martin, Haller & McClain

[57] ABSTRACT

The first purpose of the invention is to provide cordless light irradiation in which a stable amount of light is emitted when irradiating, and moreover, the device can be made compact. The second purpose is to offer a cordless light irradiation device that can control the battery temperature during use to a lower temperature than in the past.

Halogen lamp 1 equipped with a reflective mirror and batteries 4 are housed in handpiece 2. The device is equipped with battery case 3 that is provided with ventilation holes 5, cooling fan 6 and optical filter 7, and lamp guide 8 is provided on the terminal of handpiece 2.

3 Claims, 2 Drawing Sheets

CORDLESS LIGHT SOURCE

BACKGROUND OF THE INVENTION

The present invention relates to a cordless light irradiation device for the purpose of irradiating visible light or invisible light on a specific location.

In the past, there have been such cordless light irradiation light devices as that disclosed in Japanese Patent Sho 63-501054 as a light irradiation device for polymerization of composite resins for dental repair utilizing a light polymerizing type resin, but when the power source voltage drops, the surface of the resin mass is hardened, but the polymerization rate of the interior becomes insufficient, and the problem of falling out is produced.

Because the power source lamp L lights even if the voltage of the power battery B is low, the cordless light irradiation devices being currently used are structured such that a voltage observation circuit A shown in FIG. 1 is provided in the power source circuit, and switch S, by which the power voltage is supplied to the power source circuit, turns off when the battery voltage has dropped lower than a pre-set threshold voltage.

Moreover, a fan is provided for cooling the light source, but because the battery housing of the handpiece is tightly sealed, it is difficult to dissipate the heat of the battery, and there is the concern that the battery temperature may increase, and the performance of the battery deteriorate.

SUMMARY OF THE INVENTION

The first problem this invention attempts to solve is to provide a cordless light irradiation device in which a constant amount of light is obtained by always providing a stable voltage to the power source, and the second problem is to provide a cordless light irradiation device that does not invite battery performance deterioration by controlling the temperature increase of the battery.

To solve the first problem the present invention includes a cordless irradiation device that is equipped with a light source and a power source battery within a handpiece, and that is provided with a light guide which transmits the light of the light source from the terminal of the aforementioned handpiece to the location targeted for irradiation. The voltage applied to the light source is made to be lower than the power source voltage, and a voltage regulator is provided in the power source circuit. The cordless light irradiation device provides an essentially constant illumination level because the voltage regulator produces a constant voltage. The present invention may also include a cooling fan within the handpiece, and the battery housing may have ventilation holes. Battery life is prolonged because the fan and ventilation holes moderate the battery temperature.

DESCRIPTION OF THE PREFERRED EMBODIMENT

Figure 1:
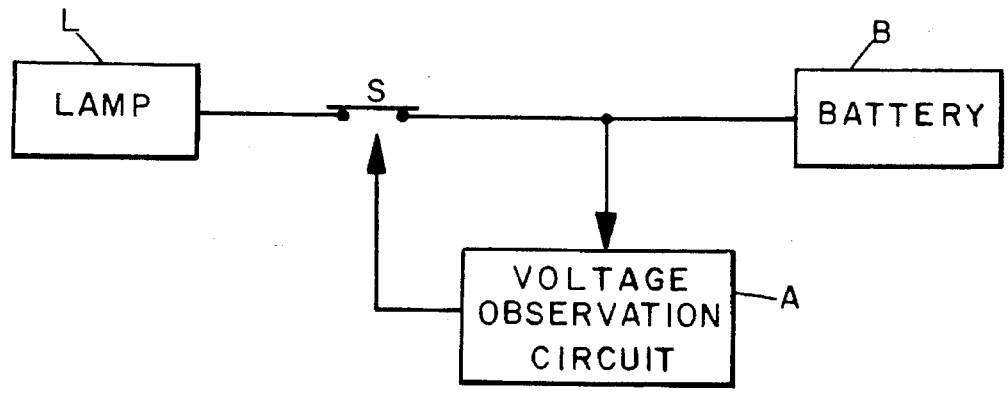
FIG. 1 is a block diagram of the electric circuit of a conventional cordless light irradiation device.
Figure 2:
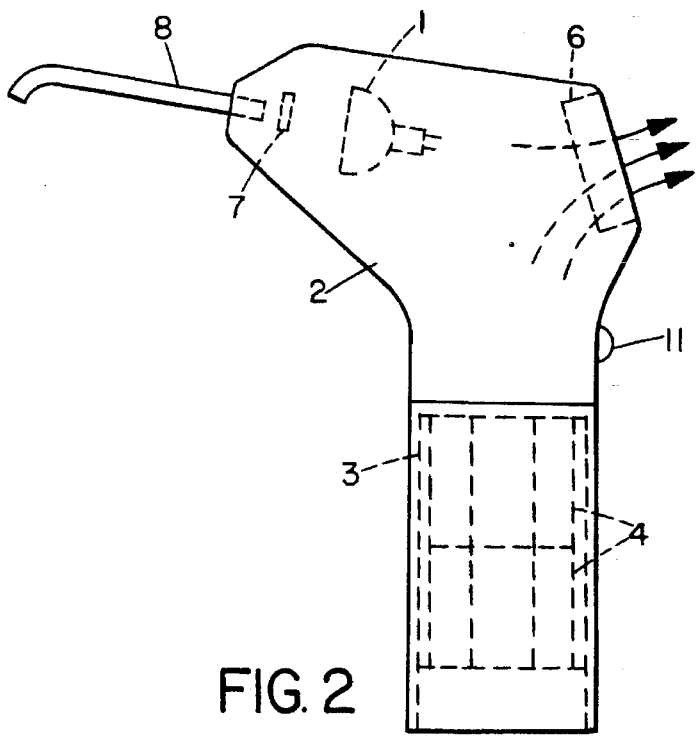
FIG. 2 is a side view of an embodiment of the present invention.
Figure 3:
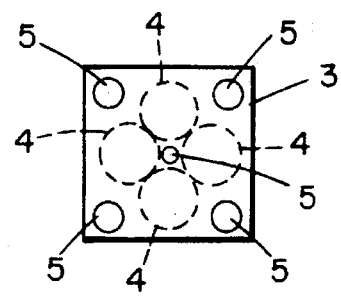
FIG. 3 is a top view of a battery case in an embodiment of the present invention.

FIG. 2 is a side view of an embodiment of the present proposal; 1 indicates a halogen lamp (light source) with a reflective mirror provided within handpiece 2; 3 is the battery case in which eight chargeable batteries 4 are housed; 5 are the ventilation holes provided on battery case 3; 6 is the cooling fan; 7 is the optical filter; and 8 is the light guide which is composed of an optical fiber bundle attached to the terminal of handpiece 2.

Figure 4:
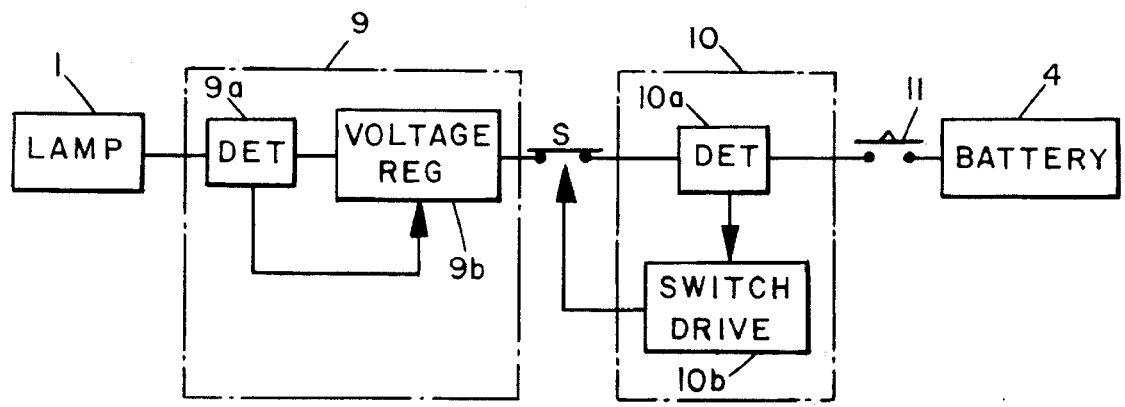
FIG. 4 is a block diagram of an electric circuit in an embodiment of the present invention.

FIG. 4 indicates a block diagram of the electric circuit; 9 is the voltage regulator which is composed of voltage detector 9a and voltage regulator circuit 9b for the purpose of keeping the applied voltage at a fixed level; 10 is the voltage observation circuit composed of voltage detector 10a, power source switch S, and switch drive circuit 10b; and voltage observation circuit 10 turns power source switch S off when the voltage falls below the set limit.

In addition, 11 in the diagram is the main switch, and in relation to the output voltage of the batteries being 9.6 V (1.2 V×8), the power source lamp utilizes an 8 volt halogen lamp which is a lower voltage rating than that of the batteries.

Because it is configured as above, when the main switch is turned on, halogen light 1 lights, a light of a specified amount of light is emitted from light guide 8, and that amount of light is maintained at a fixed level because the voltage applied on halogen lamp 1 by voltage controller 9 is always kept to a fixed level. Thus, when the battery voltage reaches a predetermined lower limit voltage of voltage regulator 9, power source switch S is turned off, and the user is informed that the batteries should be charged because the irradiation device will no longer be operable.

Figure 5:
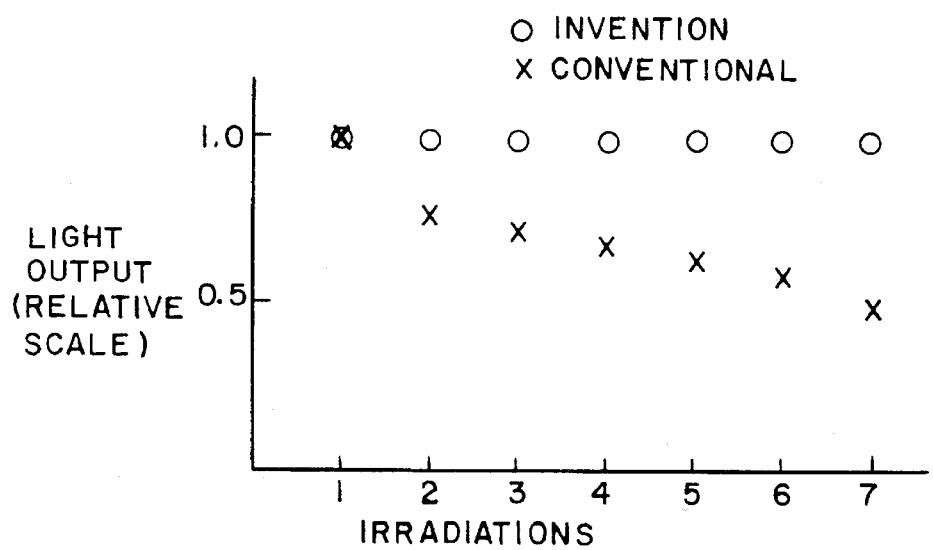
FIG. 5 is a graph indicating the changes in the amount of light in relation to the number of irradiations of a device of the present embodiment and of a conventional example.

FIG. 5 indicates the changes in the amount of light in relation to the number of irradiations for a conventional example and for this proposal when using a halogen lamp as the light source, and in the embodiment of this proposal, a stable amount of light was obtained independent of the number of irradiations.

It appears that in the conventional example, the voltage applied to the light source was lower for each irradiation, and because there are noticeable changes in the amount of light dependent on variations of the applied voltage, if a halogen lamp is used for the light source, a bigger effect is obtained.

Moreover, by making the voltage applied to the light source lower than the termination discharge voltage of the battery, the voltage regulator can be made smaller, and consequently, this is useful for making the cordless light irradiation device more compact. Moreover, because excess discharge of the battery can be prevented, the deterioration of battery performance can be controlled.

Also, because ventilation holes 5 are provided on battery housing case 3, air flows in the direction of the arrow, and a cooling effect from cooling fan 6 provided on the upper part of the battery housing is obtained. When using this structure, the temperature increase of the battery can be controlled to 80–90% compared to when there are no ventilation holes.

Until the output battery voltage reaches the input lower limit voltage of the voltage regulator, a stable voltage can be supplied to the light source, and a cordless light irradiation device that emits a stable amount of light during irradiation can be provided. Moreover, the voltage regulator is small, and consequently, the cordless light irradiation device can be made compact.

The battery temperature during use of the device can be kept to 80–90% that of the conventional devices.

Although a preferred embodiment of the invention has been described above by way of example only, it will be understood by those skilled in the field that modifications may be made to the disclosed embodiment without departing from the scope of the invention, which is defined by the appended claims.

We claim:

1. A cordless light irradiation device, comprising:

a housing having a handpiece;

a battery case within said housing, said battery case retaining batteries providing an unregulated voltage;

a voltage regulator within said housing, said voltage regulator producing a regulated voltage in response to said unregulated voltage; and a light source within said housing, said light source receiving said regulated voltage.

2. The cordless light irradiation device of claim 1, further comprising a cooling fan within said housing, and wherein said battery case has ventilation holes.

3. The cordless light irradiation device of claim 1, further comprising voltage observation means for monitoring said regulated voltage and for disconnecting electrical power from said light source when said regulated voltage falls below a predetermined lower limit.

* * * * *